(12) United States Patent
Hansson et al.

(10) Patent No.: US 11,690,946 B2
(45) Date of Patent: *Jul. 4, 2023

(54) BLOOD TREATMENT APPARATUS INCLUDING FLOW DIVIDER FOR LIMITING AN ELECTRICAL CURRENT

(71) Applicant: GAMBRO LUNDIA AB, Lund (SE)

(72) Inventors: Per Hansson, Akarp (SE); Thomas Hertz, Lund (SE); Mattias Holmer, Lund (SE); Lennart Jonsson, Bjarred (SE); Anders Nilsson, Sodra Sandby (SE); Anders Wallenborg, Bjarred (SE); Johan Andersson, Sodra Sanby (SE)

(73) Assignee: Gambro Lundia AB, Lund (SE)

( * ) Notice: Subject to any disclaimer, the term of this patent is extended or adjusted under 35 U.S.C. 154(b) by 29 days.

This patent is subject to a terminal disclaimer.

(21) Appl. No.: 17/242,877

(22) Filed: Apr. 28, 2021

(65) Prior Publication Data

US 2021/0244872 A1    Aug. 12, 2021

Related U.S. Application Data

(63) Continuation of application No. 16/667,580, filed on Oct. 29, 2019, now Pat. No. 11,000,641, which is a
(Continued)

(30) Foreign Application Priority Data

Sep. 16, 2010    (SE) .................................. 1050968-5

(51) Int. Cl.
*A61M 1/36* (2006.01)
*A61M 1/14* (2006.01)
*A61M 1/16* (2006.01)

(52) U.S. Cl.
CPC .............. *A61M 1/367* (2013.01); *A61M 1/14* (2013.01); *A61M 1/1601* (2014.02);
(Continued)

(58) Field of Classification Search
None
See application file for complete search history.

(56) References Cited

U.S. PATENT DOCUMENTS 4,155,852 A    5/1979 Fischel et al.
4,443,333 A    4/1984 Mahurkar
(Continued)

FOREIGN PATENT DOCUMENTS

DE    3512533    10/1986
EP    0458041    11/1991
(Continued)

OTHER PUBLICATIONS

Notice of Opposition filed by Fresenius Medical Care AC & Co KGaA in related EP Patent Application No. 2616117B1 on Sep. 9, 2016.
(Continued)

*Primary Examiner* — Jonathan M Peo
(74) *Attorney, Agent, or Firm* — K&L Gates LLP

(57)    ABSTRACT

A blood treatment apparatus is disclosed. The example apparatus includes a blood treatment unit including a fluid inlet and a fluid outlet and a blood line. The apparatus also includes a fluid line including an upstream fluid line configured to receive electrically conductive treatment fluid from a fluid source and pass the electrically conductive treatment fluid to the fluid inlet of the blood treatment unit and a downstream fluid line connected to the fluid outlet of the blood treatment unit for delivering the used electrically conductive treatment fluid to a fluid sink. The apparatus further includes a flow divider arranged in the downstream
(Continued)

fluid line and configured to separate the used electrically conductive treatment fluid in the downstream fluid line into to a first fluid section and a second fluid section, thereby electrically isolating the first and second fluid sections.

20 Claims, 4 Drawing Sheets

Related U.S. Application Data continuation of application No. 13/824,892, filed on Aug. 14, 2013, now Pat. No. 10,493,197.

(52) U.S. Cl.
CPC ... *A61M 1/3621* (2013.01); *A61M 2205/3317* (2013.01); *A61M 2205/3334* (2013.01); *A61M 2205/50* (2013.01); *Y10T 29/49002* (2015.01)

(56) References Cited

U.S. PATENT DOCUMENTS

| | | | |
|---|---|---|---|
| 5,578,223 A | 11/1996 | Bene et al. | |
| 5,736,038 A | 4/1998 | Stoughton | |
| 6,136,201 A | 10/2000 | Shah et al. | |
| 6,663,585 B1 * | 12/2003 | Ender | A61M 5/16831 210/645 |
| 8,180,443 B1 | 5/2012 | Kleinekofort | |
| 2003/0195453 A1 | 10/2003 | Han | |
| 2003/0209475 A1 | 11/2003 | Connell et al. | |
| 2003/0218623 A1 | 11/2003 | Krensky et al. | |
| 2003/0220598 A1 | 11/2003 | Busby et al. | |
| 2004/0019312 A1 | 1/2004 | Childers | |
| 2004/0267183 A1 | 12/2004 | Chevallet | |
| 2005/0045540 A1 | 3/2005 | Connell et al. | |
| 2005/0131332 A1 | 6/2005 | Kelly | |
| 2006/0177351 A1 | 8/2006 | Heiniger et al. | |
| 2008/0065006 A1 | 3/2008 | Roger et al. | |
| 2009/0177149 A1 | 7/2009 | Childers et al. | |
| 2010/0022935 A1 * | 1/2010 | Muller | A61M 1/3661 604/6.04 |
| 2010/0312161 A1 | 12/2010 | Jonsson | |

FOREIGN PATENT DOCUMENTS

| | | | |
|---|---|---|---|
| EP | 0611228 | 8/1994 | |
| EP | 0 820 776 | 1/1998 | |
| JP | 10-24192 | 1/1998 | |
| JP | 10-85323 | 4/1998 | |
| WO | 9306875 | 4/1993 | |
| WO | 9411093 | 5/1994 | |
| WO | 99/12588 | 3/1999 | |
| WO | 2005044339 | 5/2005 | |
| WO | 2008031539 | 3/2008 | |
| WO | WO-2008031539 A1 * | 3/2008 | .......... A61M 1/3653 |
| WO | 2009044220 | 4/2009 | |
| WO | WO-2009044220 A1 * | 4/2009 | ............. A61M 1/16 |
| WO | 2010011441 | 1/2010 | |
| WO | 2010077762 | 7/2010 | |

OTHER PUBLICATIONS

Eidesstattliche Versicherung von Herm Dr. Jorg Dreyhsig. Affidavit of Dr. Jorg Dreyhsig asserting the booklet referred to as D13 (Fresenius Medical Care: Prospekt: Acute Therapy Systems: multiFiltrate, 2006) was available to the public at the ERA-EDTA conference in Glasgow, UK in 2006. D13.

DIN EN 60601-1 (VDE 0750-1), Seiten 84-87 (Jul. 2007). Medical electrical equipment—Part 1 : General requirements for basic safety and essential performance (IEC 60601-1 :2005); German version EN 60601-1:2006. D16.

C. Ronco et al., "Critical Care Nephrology," Kluwer Academic Publishers, 1998. 7 pages. D12.

Ansiiaami ES1-1993. American National Standard. Current safe limits for electromedical apparatus. Developed by Association for the Advancement of Medical Instrumentation. Dec. 2, 1993. D15.

P. Jonsson et al., Blood Lines Conduct Leakage Current During Haemodialysis: A Potential Safety Risk During First Failure, Especially for Patients with Central Dialysis Catheter as Access, Medical & Biological Engineering & Computing 2005, vol. 43, No. 6, pp. 731-738.

EP Decision on Appeal No. T0385/18-3.2.02; Opponent Fresenius Medical Care AG & Co. KGaA mail date Nov. 9, 2022—26 pages.

* cited by examiner

BLOOD TREATMENT APPARATUS INCLUDING FLOW DIVIDER FOR LIMITING AN ELECTRICAL CURRENT

PRIORITY CLAIM

The present application is a continuation of U.S. application Ser. No. 16/667,580, filed Oct. 29, 2019, now U.S. Pat. No. 11,000,641, entitled, "BLOOD TREATMENT APPARATUS INCLUDING FLOW DIVIDER FOR LIMITING AN ELECTRICAL CURRENT", which is a continuation of U.S. application Ser. No. 13/824,892, filed Aug. 14, 2013, now U.S. Pat. No. 10,493,197, entitled, "BLOOD TREATMENT APPARATUS WITH FLOW DIVIDER FOR LIMITING AN ELECTRICAL CURRENT", which is a national stage entry of PCT Application No. PCT/EP2011/065894, filed Sep. 14, 2011 and published as PCT Publication No. WO2012/035040 on Mar. 22, 2012, which claims priority to U.S. Provisional Application No. 61/383,374, filed Sep. 16, 2010, and Swedish Patent Application No. 1050968-5, filed Sep. 16, 2010, the entire contents of each of which are incorporated herein by reference and relied upon.

TECHNICAL FIELD

The invention relates to an apparatus with a blood treatment unit through which electrically conductive treatment fluid is passed for treating blood.

BACKGROUND

Today blood treatment apparatuses are used for extracorporeal blood treatment and involves drawing blood from a patient, treating the blood and returning the treated blood to the patient. For this purpose an extracorporeal blood flow circuit is used which is connected to a blood vessel access of the patient, typically via one or more access devices such as needles or cannulas inserted into the blood vessel access. Depending on method of blood treatment, the blood may be withdrawn and returned via the same blood vessel access or via separate blood vessel accesses. Extracorporeal blood treatment includes hemodialysis, hemodiafiltration, hemofiltration, plasmapheresis etc.

The blood treatment apparatus is in principle an electrically powered machine that is fed with an electrical current. If an electrical failure occurs in the blood treatment apparatus, there might be a risk that the patient is subjected to an electrical shock which may have severe consequences. Thus, it is vital that the blood treatment apparatus is designed such that it offers a high degree of electrical insulation for reducing the risk that an electrical current flows from the apparatus, via the extracorporeal blood circuit and access device and into the patient.

This problem has been addressed, for example in WO2009/044220 A1 where a blood treatment apparatus includes a membrane device that comprises a blood chamber and a fluid chamber separated by a semipermeable membrane. A grounding device is connected to a treatment fluid discharge line by means of a tubular connector made of an electrically-conductive plastic material. The grounding device can disconnect the grounding connection if a leakage current measured on a patient connected to the apparatus exceeds a predetermined value.

Further prior art is reflected by US2009177149 A1 where various kinds of leakage currents are addressed, and by U.S. Pat. No. 4,155,852 A which relates to a blood treatment apparatus that incorporates an electrically isolated flux heater.

The techniques mentioned above are generally capable of reducing the risk of a patient being subject to an electrical shock. However, it is believed that the risk can be further reduced in case a blood treatment apparatus experiences an electrical failure. This is particularly relevant when the blood treatment apparatus is intended for home use, where relatively higher safety requirements typically are required.

SUMMARY

It is an object of the invention to at least partly overcome one or more limitations of the prior art. In particular, it is an object to provide a blood treatment apparatus that may reduce the risk of a patient being subjected to electrical shock if an electrical failure occurs.

Hence a blood treatment apparatus is provided, which comprises: a blood treatment unit; a blood line configured to extract blood from a blood source, pass the blood through the blood treatment unit and deliver treated blood to a target vessel; a fluid line configured to extract electrically conductive treatment fluid from a fluid source, pass the treatment fluid through the blood treatment unit and deliver used treatment fluid to a fluid sink; and a flow divider arranged in the fluid line and configured to separate treatment fluid in the fluid line into to a first fluid section and a second fluid section, thereby electrically isolating the fluid sections such that electrical current flowing in the fluid line between the fluid sections is limited.

Limiting the electrical current may here include completely preventing an electrical current from flowing between the sections. By electrically isolating the fluid sections a grounding connection to the fluid sink is broken. Since this grounding connection is broken, a patient connected to the apparatus is electrically floating in the sense that there is no connection that may pass a current through the patient. Thereby is the risk of subjecting the patient to an electrical shock significantly reduced.

In this context, it should be noted that the sink is generally the only item that connects a typical blood treatment apparatus to the ground, and that common treatment fluids are electrically conductive. This is also true for configurations were water is drawn from a water source and mixed with a concentrate to form the treatment fluid, since the water is typically de-ionized and thereby not electrically conductive.

Electrically isolating the fluid sections may be understood as preventing a predetermined current from flowing between the fluid sections of the fluid that is conveyed within the fluid line. This predetermined current must not be zero but may not exceed a value that is harmful for a patient. Thus, the flow divider is developed with the intention to electrically isolate the fluid sections. From this follows that the flow divider is intentionally configured to prevent a patient connected to the blood treatment apparatus from being subjected to electrical shock. For this purpose the flow divider may be of a type that has been verified for assuring that it provides electrical isolation. The electrical isolation may typically comprise isolation that assures that a patient may not be subjected to a harmful electrical shock. It may also be said that the flow divider is of a type that has been verified for its capability to reduce or prevent a current from flowing between the fluid sections. In any case, the electrical isolation provided by the flow divider is both known and intentional. Of course, the flow divider may incorporate more functionality than the electrical isolation of fluid sections, such as the function of transporting fluid in the fluid sections.

The electrical isolation provided by the flow divider may not be seen as an "accidental" or implicit electrical isolation that is achieved by a component arranged in the fluid line without the intentional purpose of providing the electrical isolation. This is true since "accidental"/implicit electrical isolation does not mean that a patient in fact is protected from an electrical shock.

As will be described below, the flow divider may be of several types which have all verified for assuring that electrical isolation is provided.

An advantage with the blood treatment apparatus lies in that a patient is proactively protected from electrical shock, in comparison with other systems that have a more reactive character in the sense that protection is initiated after a fault has occurred, i.e. when a patient already may have suffered some injury.

The fluid line may comprise an upstream fluid line and a downstream fluid line, where the downstream fluid line is connected to a fluid outlet of the blood treatment unit for delivering the used treatment fluid to the fluid sink, and wherein the flow divider is arranged in the downstream fluid line.

The flow divider may be configured to separate the treatment fluid in the fluid line into multiple fluid sections, thereby breaking up a flow of treatment fluid in the fluid line.

The flow divider may be configured to provide a gas gap in the fluid line for generating the separation of the treatment fluid. Typically, the gas may be air that is drawn form the environment surrounding the blood treatment apparatus.

The flow divider may be configured to periodically open and close the fluid line for generating the separation of the treatment fluid. This may, for example, mean that the flow divider is configured to periodically open and close the fluid line by periodically compressing and thereby occluding the fluid line.

The flow divider may comprise a drip chamber for generating the separation of the treatment fluid.

The flow divider may comprise a first opening device and a second opening device, the opening devices configured to periodically open and close the fluid line for generating the separation of the treatment fluid. The first and second flow dividers may be arranged in series or in parallel in the fluid line. When arranged in parallel the flow dividers are typically arranged in a respective branch line of the fluid line. Examples of opening devices include e.g. valves, pump and clamps, i.e. at least one of the opening devices may comprise a clamp, valve and/or pump.

The flow divider may comprise a peristaltic pump for generating the separation of the treatment fluid. The peristaltic pump may comprise at least two rollers configured to periodically compress the fluid line. The peristaltic pump may be referred to as a roller pump, and the rollers may be referred to as a "shoes" or "wipers". The peristaltic pump electrically isolates the fluid sections such that electrical current flowing in the fluid line between the fluid sections is limited. As previously indicated, the electrical isolation is deliberately provided and is thus intentional. This means that the peristaltic pump may be of a peristaltic pump type that has been verified in respect of its capability of providing electrical isolation. This is also true for the general flow divider described above, i.e. the flow divider may be of a flow divider type that has been verified in respect of its capability of providing electrical isolation.

The fluid line may comprise a buffer chamber configured to cooperate with the flow divider, for generating the separation of the treatment fluid in the fluid line.

The flow divider may be configured to electrically isolate the first and second fluid sections such that the electrical current is limited to a predetermined value. Specifically, the flow divider may be configured to electrically isolate the first and second fluid sections such that the electrical current is limited to maximum 500 µA, 50 µA or 10 µA.

The blood treatment apparatus may comprise a control unit configured to measure an electrical voltage over a section of the fluid line downstream the flow divider. More specifically, the control unit may be configured to verify that the measured electrical voltage is below a predetermined value.

Also, the blood treatment apparatus may comprise a control unit configured to verify (i.e. measure) if an electrical current flows between the first and second fluid sections. In principle, measuring a voltage and verifying a current are here functionally equivalent.

In further detail, the control unit may comprise a first connector arranged in the fluid line upstream the flow divider and a second connector arranged in the fluid line downstream the flow divider, such that the control unit may apply a voltage over the connectors and determine a current thereby flowing in the treatment fluid between the connectors. Applying a voltage and determining a current is here equivalent to feeding a current between the first connector and the second connector and determining a resulting voltage there over.

As an addition or alternative to the connectors upstream and downstream the flow divider, the control unit may comprise two connectors downstream the flow divider and the control unit may then be configured to measure a voltage over the two downstream connectors. This measurement may be continuous or intermittent, and, if a measured voltage is above a predetermined value, the control unit may initiate a signal that indicates that the flow divider does not longer provide the desired electrical isolation.

The control unit may be configured to monitor if the current exceeds a predetermined current value. This is equivalent to monitoring if a voltage is below a predetermined voltage value (for the above equivalent case of feeding a current between the connectors and determining a resulting voltage there over).

The control unit may be configured to break a power supply to the blood treatment apparatus, if the current exceeds the predetermined current value (or if the voltage is below a predetermined voltage in the equivalent case).

A previously indicated, the flow divider may be of a flow divider type that has been verified in respect of its capability of providing electrical isolation. Being verified may typically involve arranging the flow divider in a fluid line, applying a voltage over the flow divider and measuring if an electrical current passes the flow divider as a result of the applied voltage. Other, corresponding verification methods may be used just as well.

According to another aspect a method is provided for manufacturing the blood treatment apparatus described above, including all embodiments thereof. The manufacturing comprises the step of arranging the flow divider in the fluid line of the blood treatment apparatus, wherein the manufacturing of the blood treatment apparatus has been preceded by a verification that the flow divider is of a type that separates treatment fluid in the fluid line into to the first fluid section and the second fluid section, such that the flow divider electrically isolates the fluid sections and thereby limits any electrical current flowing in the fluid line between the fluid sections.

The method of manufacturing includes steps for arranging all other components comprised in the blood treatment apparatus. However, the manufacturing is always preceded by the verification of the flow divider.

The verification preceding the manufacturing may include verifying that the flow divider electrically isolates the fluid sections such that the electrical current is limited to maximum any of 500 µA, 50 µA and 10 µA.

According to another aspect a method is provided for verifying a flow divider, the flow divider configured to be arranged in a fluid line of a blood treatment apparatus and to separate treatment fluid in the fluid line into a first fluid section and a second fluid section, thereby electrically isolating the fluid sections such that electrical current flowing in the fluid line between the fluid sections is limited. The method comprises the steps of: applying a voltage over a first connector and a second connector, the first connector arranged in the fluid line upstream the flow divider and the second connector arranged in the fluid line downstream the flow divider; and measuring a current resulting from the applied voltage. The verification method may comprise verifying that the electrical current is limited to maximum any of 500 µA, 50 µA and 10 µA.

The described method of verification is equivalent to verifying if a voltage downstream the flow divider is below a predetermined level. More specifically, then the method may comprise the steps of: feeding a current through the flow divider; and measuring a voltage over a first connector and a second connector, where both connectors are arranged in the fluid line and downstream the flow divider.

The various methods may include any of the features described above in association with the blood treatment apparatus and shares the corresponding advantages. Still other objectives, features, aspects and advantages of the invention will appear from the following detailed description, from the attached claims as well as from the drawings.

BRIEF DESCRIPTION OF THE DRAWINGS

Embodiments of the invention will now be described, by way of example, with reference to the accompanying schematic drawings, in which.

DETAILED DESCRIPTION OF THE PRESENT DISCLOSURE

Figure 1:
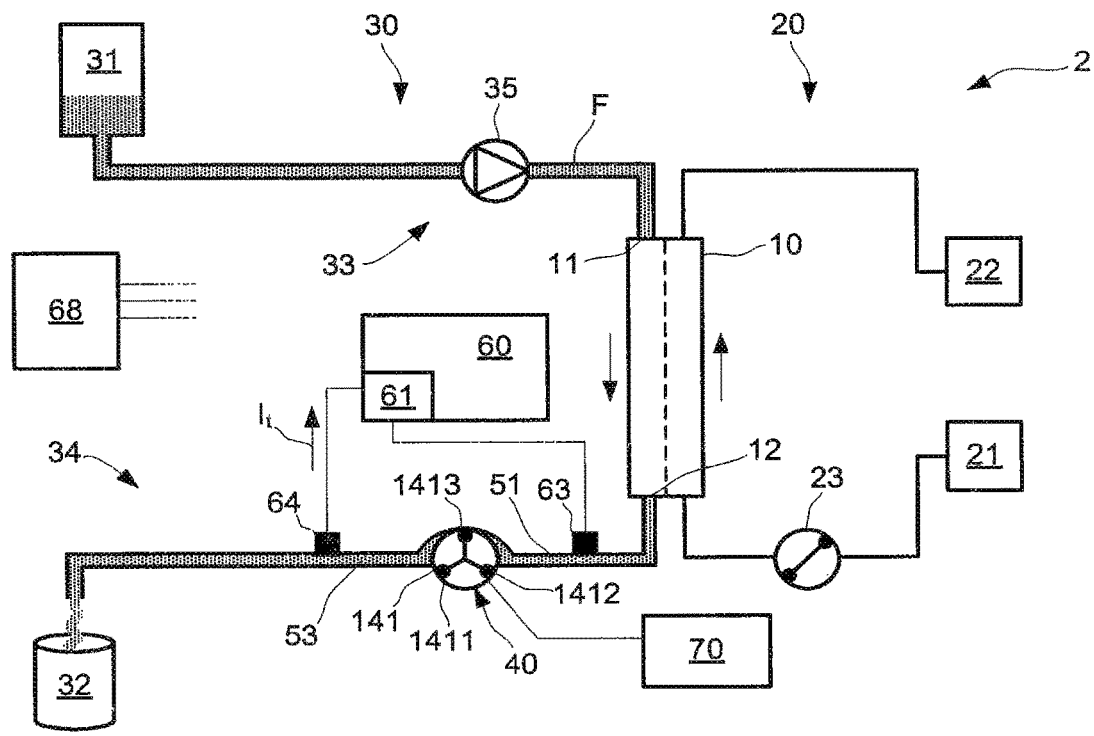
FIG. 1 illustrates a blood treatment apparatus according to a first embodiment.

With reference to FIG. 1 a blood treatment apparatus 2 for extracorporeal blood treatment is illustrated. The blood treatment apparatus 2 comprises a blood treatment unit 10 and a blood line 20 with a blood pump 23 arranged to draw blood from a blood source 21, pass the blood through the blood treatment unit 10 (which then may treat the blood) and deliver the treated blood to a target vessel 22. The configuration of the blood line 20 and the blood treatment unit 10 is implemented according to known techniques and may include various other components and control units generally used in blood treatment apparatuses. The blood source 21 and target vessel 22 may be a patient that receives blood treatment but may also be bags of blood that are handled by operators.

The blood treatment apparatus 2 has also a fluid line 30 arranged to draw treatment fluid (dialysate) from a fluid source 31, pass the treatment fluid through the blood treatment unit 10 and deliver used treatment fluid to a fluid sink 32. The fluid sink 32 may, for example, be a drain or sewer.

Within the blood treatment unit 10 the treatment fluid interacts with the blood in a manner known within the art, such that the treated blood may be delivered to the target vessel 22. The fluid line 30 is divided into an upstream fluid line 33 with a fluid pump 35 that delivers treatment fluid to the blood treatment unit 10, and a downstream fluid line 34 connected to the fluid sink 32. Thus, the upstream fluid line 33 is connected to a fluid inlet 11 of the blood treatment unit 10 while the downstream fluid line 34 is connected to a fluid outlet 12 of the blood treatment unit 10.

The downstream fluid line 34 comprises a flow divider 40 that is arranged to separate (used) treatment fluid in a first fluid section 51 and a second fluid section 53. Even though the fluid sections 51, 53 are separated they are still within the downstream fluid line 34 in the sense that the fluid composing the fluid sections 51, 53 are conveyed inside the fluid line 30. The flow divider 40 is in the illustrated embodiment a peristaltic pump 141 that periodically occludes the downstream fluid line 34, which in this case may be made of a flexible plastics material that may be compressed while it regains its original shape after the compression is released. The upstream fluid line 33 may be made of the same material, which has electrically isolating properties, such as materials like PVC, silicon rubber, thermoplastic elastomer etc. The occlusion separates the fluid in to the first fluid section 51 and the second fluid section 53, where the point of separation is defined by the location where the peristaltic pump 141 occludes the downstream fluid line 34.

The peristaltic pump 141 comprises a first roller 1411, a second roller 1412 and a third roller 1413 that compress the downstream fluid line 34. The downstream fluid line 34 is arranged around the peristaltic pump 141 such that at least one roller always fully compresses the downstream fluid line 34. Thus, when one of the roller starts to release an occluding pressure on the downstream fluid line 34, the next roller has already achieved full compression of the downstream fluid line 34. It may hence be assured that the fluid is always separated into (at least) a first fluid section 51 and a second fluid section 53.

The peristaltic pump 141 is not an ordinary peristaltic pump even though its principle layout may correspond to conventional peristaltic pumps. In detail, the peristaltic pump 141 is developed with the purpose of assuring that an electric current flowing from the first fluid section 51 to the second fluid section 53 is limited or prevented. The peristaltic pump 141 is therefore of a type that has been verified in respect of its capability of providing electrical isolation.

In detail, the flow divider 40 is configured to electrically isolate the first and second fluid sections such that the electrical current is limited to maximum 500 µA, 50 µA or 10 µA. These figures apply for all embodiments of a flow divider described herein as well as for other conceivable flow dividers.

The peristaltic pump 141 as well as the more general flow divider 40 may be controlled by a control device 70 for obtaining e.g. a proper occlusion of the downstream fluid line 34. In this particular embodiment the peristaltic pump 141 may be used as a mean for transporting the treatment fluid through fluid line 30, and the control device 70 may also control the flow rate.

Figures 2A, 2B:
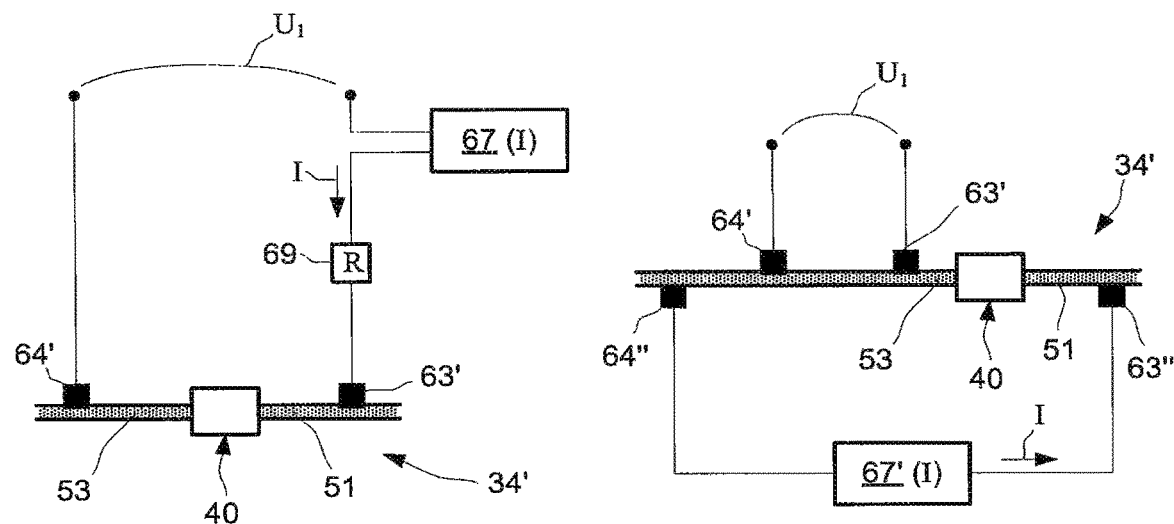
FIG. 2a illustrates a test configuration for verifying that a flow divider electrically isolates two fluid sections.
FIG. 2b illustrates an alternative test configuration that is functionally equivalent with the test configuration of FIG. 2a, FIG. 3 illustrates a blood treatment apparatus according to a second embodiment.

With further reference to FIG. 2a an illustration is given of a test configuration for verifying that the flow divider 40, e.g. in the form of the peristaltic pump 141, electrically isolates the fluid sections 51, 53. The test configuration is set up for a fluid line 34' that corresponds to the downstream fluid line 34 of FIG. 1, by arranging the flow divider 40 in the fluid line 34' between a first connector 63' and a second connector 64'. A voltage $U_1$ is applied over the connectors 63', 64' and the test configuration includes a resistor 69 with a resistance R. The applied voltage $U_1$ may be an AC voltage or DC voltage, and may be galvanically isolated (floating). A current meter 67 measures a current I flowing in the illustrated circuit, which then is the current flowing from the first connector 63', through the flow divider 40 and to the second connector 64'. The measured current is zero (0) in case the flow divider provides complete electrical isolation.

The configuration of FIG. 2a can be verified for assuring that it operates properly, for example by connecting a cable between the connectors 63', 64' such that the current I may flow there between.

An alternative embodiment of the test configuration may also be used, which has four connectors to the fluid path; two for applying a current and two for measuring voltage, in a so called 4-point measurement. One current connector and one voltage connecter is then placed on each side of the flow divider.

With reference to FIG. 2b another embodiment of a test configuration is shown, which is functionally equivalent with the configuration of FIG. 2a. This test configuration is set up for a fluid line 34' by arranging the flow divider 40 upstream two connectors 63', 64' over which a voltage $U_1$ may be measured. A current unit 67' is connected to a first current connector 63" and to a second current connector 64" arranged on a respective side of the flow divider 40, for feeding a current I through the flow divider 40. If the measured voltage $U_1$ is zero, then the flow divider 40 provides complete electrical isolation.

By using the test configuration of FIG. 2a the peristaltic pump 141 of FIG. 1 that electrically isolates the fluid sections 51, 53 may be properly configured or adjusted. In detail, the occluding force exerted by the rollers 1411-1413 on the fluid line 34 is adjusted such that the current I is minimized. When performing tests and adjusting the peristaltic pump 141, it could be shown that the peristaltic pump 141 may isolate the fluid sections 51, 53 to that extent that the current I never exceeded 8 µA. Depending on the position of the rollers 1411-1413, it was observed that the measured current varied between 0-8 µA. Also, when the flow divider is a roller pump then the test configuration may be employed for verifying if the roller pump occludes properly, e.g. at start up (so called priming) of the blood treatment apparatus.

As an alternative to using a peristaltic pump, any suitable type of pump may be used as long as it operates in a manner that always keep the sections 51, 53 separated such that electrical isolation is assured (i.e. verified). Examples of principal types of pumps that may be used include positive displacement pumps (such as gear pumps, rotary vane pumps and roller pumps) and reciprocating-type pumps (such as piston pumps, diaphragm pumps). Such pumps must of course be verified as described above as well as (most likely) adjusted for increasing the level of separation. In other words, conventional pumps (i.e. unverified pumps) may not be used since they do not electrically isolate the fluid sections 51, 53 in the sense required herein.

Turning back to FIG. 1, as an alternative, the blood treatment apparatus 2 may include a control unit 60 that may apply a voltage over a first connector 63 and a second connector 64. The first connector 63 is connected to the downstream fluid line 34 at a position upstream the flow divider 40, while the second connector 64 is connected to the downstream fluid line 34 at a position downstream the flow divider 40. The connectors 63, 64 are in electrical contact with the treatment fluid but do not obstruct the flow of treatment fluid, and does not allow any treatment fluid to escape from the fluid line 30. The control unit 60 applies a voltage via a combined voltage source and current meter 61. The voltage source/current meter 61 operates in a manner similar to the circuit shown in FIG. 2a.

During operation of the blood treatment apparatus 2 the rollers 1411-1413 of the peristaltic pump 141 ensure that the fluid line 30 is always occluded at a varying position. When the fluid line 30 is occluded, the walls of the fluid line 30 meet each other and thereby separate the treatment fluid. Since the fluid line 30 is made of an electrically isolating material no current or a maximum current of 8 µA passes between the separated fluid sections 51, 53. From this follows that an electrical ground with the fluid sink 32 is in principle broken which significantly decreases the risk of being subjected to electrical shock, for example if some component of the blood treatment apparatus 2 malfunctions such that an electrical current may be transferred to a patient, for example via the blood treatment unit 10 and the blood line 20.

Also, during the operation the control unit 60 applies via the voltage source/current meter 61 a voltage over the first connector 63 and the second connector 64. The voltage source/current meter 61 provides a reading of any current flowing between the connectors 63, 64 via the flow divider 40. The voltage is either continuously or at regular time intervals applied over the connectors 63, 64 and if a current $I_t$ is detected a proper action may be taken. For example, if the current is above 10 µA, 50 µA or 500 µA the control unit 60 may break a power supply 68 to the blood treatment apparatus 2. The power supply 68 is typically a conventional current source that feeds the blood treatment apparatus 2 with an electrical current. The control unit 60 provides additional safety in that the flow divider 40 may be regularly verified in terms of its capability to electrically isolate the fluid sections 51, 53. A suitable voltage value to apply generally depends on what current level shall be measured, on the type of flow divider 40 used as well as on other components of the blood treatment unit. A suitable interval for the verification may be each time the blood treatment apparatus 2 is prepared for treatment of a new patient.

It should be observed that the control unit 60 does not replace the verification that the flow divider 40 is of a type that provides electrical isolation. Instead, the verification performed by the control unit 60 is an additional safety precaution that is performed for the flow divider 40 that is a part of the blood treatment apparatus 2.

It should also be understood that the voltage source/current meter 61 is equivalent to a unit that may send a current through the connectors 63, 64 via the flow divider 40 and measure a resulting voltage, in which case the control unit 60 may e.g. break the power supply to the blood treatment apparatus 2 if the voltage is below a predetermined value. Here, applying a voltage and measure a resulting current is functionally the same as feeding a current and measuring a resulting voltage.

Figure 3:
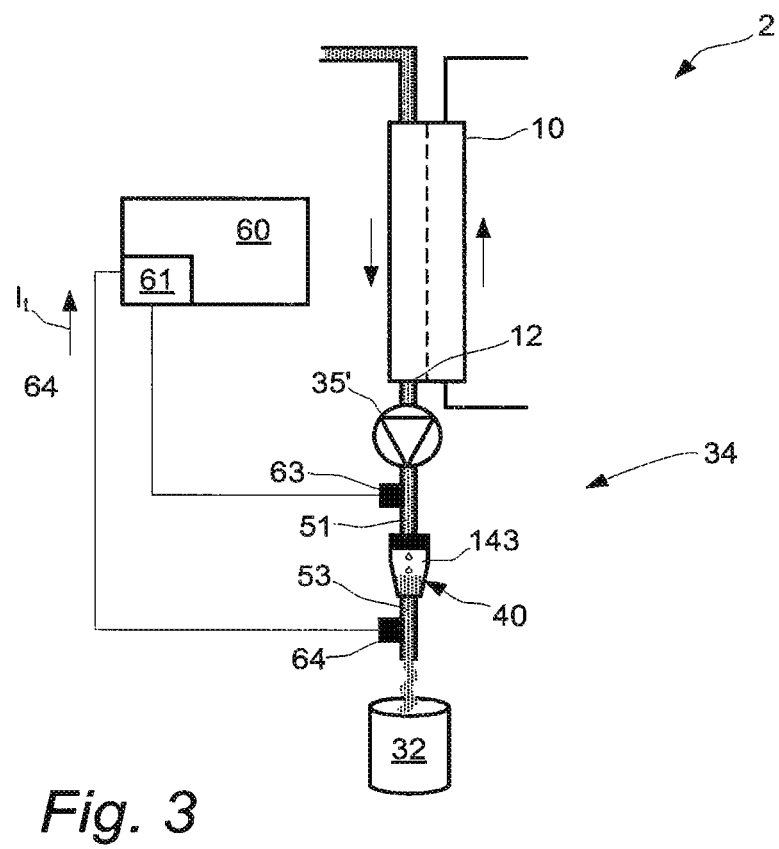

With reference to FIG. 3 another embodiment of a flow divider 40 is illustrated. In this case the flow divider 40 comprises a drip-chamber 143 that separates the treatment fluid into the first fluid section 51 and second fluid section 53 by forming drops in the drip-chamber 143. The drip-chamber 143 may here comprise all shower-like structures, including configurations that are open to the surrounding environment (i.e. without a closed or sealed drip chamber).

A pump 35' is arranged upstream the drip-chamber 143. Apart from the pump 35' and the flow divider 40 being a drip-chamber 143, the other components are the same as in the blood treatment apparatus 2 of FIG. 1. For this reason the complete blood treatment apparatus 2 is not illustrated in FIG. 3, but only the downstream fluid line 34.

The drip-chamber 143 is not an ordinary drip-chamber even though its principle layout and principles of operation may correspond to conventional drip-chambers. In detail, the drip-chamber 143 is developed for the purpose of assuring that an electric current flowing from the first fluid section 51 to the second fluid section 53 is limited. The drip-chamber 143 is therefore of a type that has been verified in respect of its capability of providing electrical isolation. This includes adjusting e.g. the drip-forming rate and drip height so that any current flowing between the fluid sections 51, 53 is properly limited.

Figure 4:
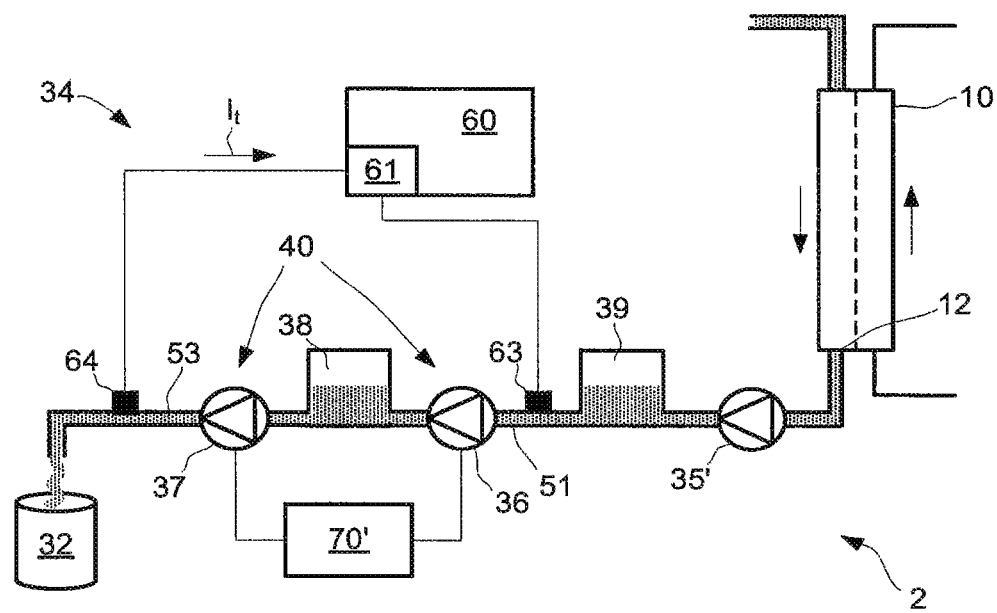
FIG. 4 illustrates a blood treatment apparatus according to a third embodiment.

With reference to FIG. 4 another embodiment of a flow divider 40 is illustrated. In this case the flow divider 40 comprises a first flow stopper 36 and a second flow stopper 37. The flow stoppers 36, 37 are arranged in series in the downstream fluid line 34, and a first buffer chamber 39 is arranged between the blood treatment unit 10 and first flow stopper 36 while a second buffer chamber 38 is arranged between the flow stoppers 36, 37. The flow stoppers 36, 37 may be e.g. pumps, valves or clamps that may be opened and closed by a control device 70'. The downstream fluid line 34 may include a pump 35' arranged upstream the flow divider 40, for transporting the treatment fluid forwards towards the fluid sink 32.

In operation, the control device 70 intermittently opens and closes the flow stoppers 36, 37 such that the treatment fluid may flow intermittently from the blood treatment unit 10 to the fluid sink 32. However, before one flow stopper is opened the other is closed, and thereby the treatment fluid is always separated into the first fluid section 51 and the second fluid section 53.

Apart from the flow divider 40 in form of the flow stoppers are other parts of the blood treatment apparatus in this embodiment similar with the blood treatment apparatus 2 illustrated in FIG. 1. The flow divider 40 is in this embodiment developed with the purpose of assuring that an electric current flowing from the first fluid section 51 to the second fluid section 53 is limited. Thus, even though the flow stoppers 36, 37 may have the principal form of a conventional pump, clamp or valve, the flow stoppers 36, 37 (pumps/clamps/valves) are not of commonly known types since they are developed with the purpose of assuring that an electric current flowing from the first fluid section 51 to the second fluid section 53 is limited. The flow stoppers 36, 37 (pumps/clamps/valves) are therefore of a type that has been verified in respect of its capability of providing electrical isolation. This includes adjusting e.g. the closing or occluding properties of the flow stoppers so that any current flowing between the fluid sections 51, 53 is properly limited.

Tests have been performed by using clamps as flow stoppers that occlude the downstream fluid line 34 at sections made of the flexible material discussed in connection with FIG. 1. Such tests show that the fluid sections 51, 53 may be separated to the extent that no electrical current at all may flow between them. Similar results have been obtained when properly adjusting the flow stopping properties of a 2-way 24 V magnet valve.

Figure 5:
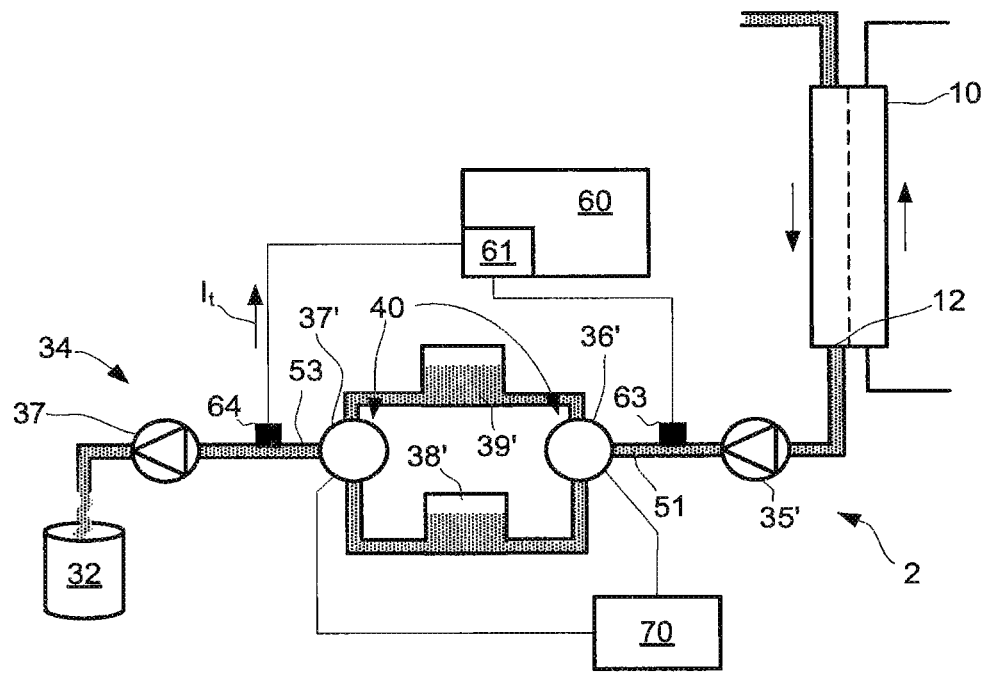
FIG. 5 illustrates a blood treatment apparatus according to a fourth embodiment.

With reference to FIG. 5 another embodiment of a flow divider 40 is illustrated. In this case the flow divider 40 comprises a first 3-way valve 36' and a second 3-way valve 37'. The downstream fluid line 34 comprises a pump 35' upstream the flow divider, a first buffer chamber 38' and a second buffer chamber 39' arranged in parallel, as can be seen in the figure. Apart from this the blood treatment apparatus 2 is similar with that of FIG. 1.

During operation the 3-way valves 36', 37' are controlled by the control device 70 in that the first 3-way valve 36' feeds treatment fluid to the first buffer chamber 38' when the second 3-way valve 37' draws treatment fluid form the second buffer chamber 39'. Thereafter the first 3-way valve 36' feeds treatment fluid to the second buffer chamber 39' while the second 3-way valve 37' draws treatment fluid form the first buffer chamber 38'. Before changing to/from which buffer chamber treatment fluid is fed/drawn, the 3-way valves are fully closed and thereby the first fluid section 51 and the second fluid section 53 are always separated. The separation provides electrical insulation between the fluid sections 51, 53, and the two 3-way valves 36', 37' are developed with the purpose of limiting an electric current flowing from the first fluid section 51 to the second fluid section 53. Thus even though the 3-way valves 36', 37' may have a principal form of a conventional 3-way valve, they are not of a commonly known type since they are developed with the purpose of assuring the limitation of an electrical current.

Figure 6:
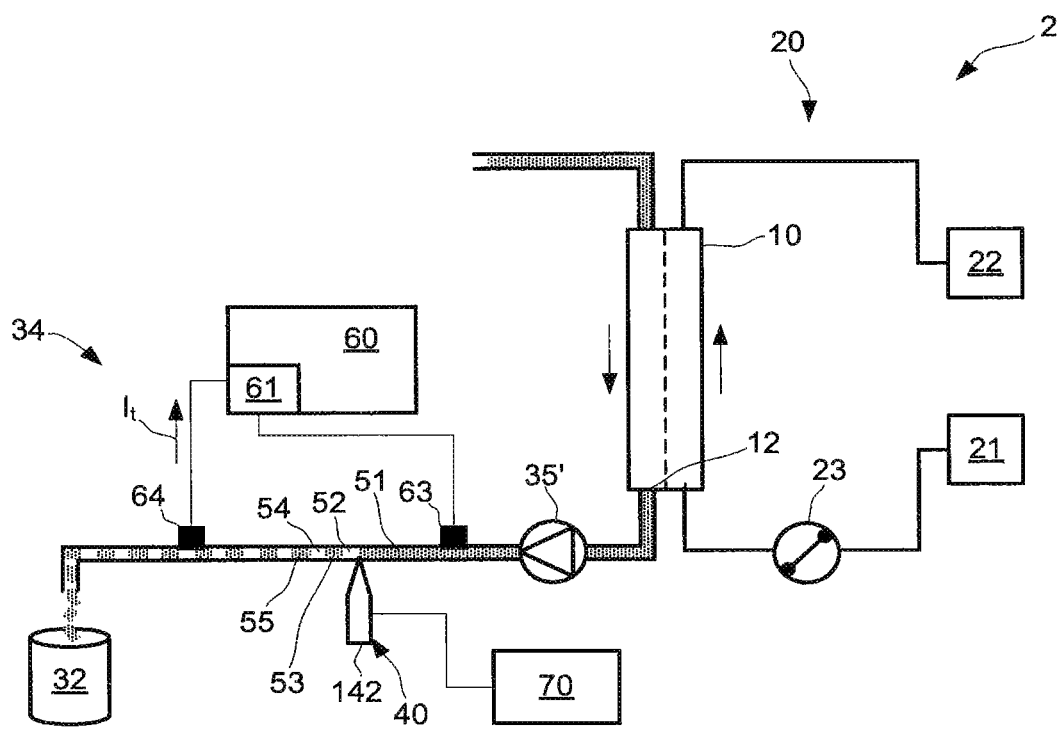
FIG. 6 illustrates a blood treatment apparatus according to a fifth embodiment.

With reference to FIG. 6 another embodiment of a flow divider 40 is illustrated. In this case the flow divider 40 comprises an air injector 142 that is controlled by the control device 70 to blow air or another gas into the downstream fluid line 34. A pump 35' is arranged upstream the flow divider 40, in the downstream fluid line 34. During operation air is blown/injected into the downstream fluid line 34 at regular intervals such that a number of air (gas) gaps 52, 54 are created. The air gaps 52, 54 separate the treatment fluid into a number of sections 51, 53, 55, for example into the first fluid section 51 and the second fluid section 53.

The flow divider 40 in form of the air injector 142 is developed with the purpose of limiting an electrical current flowing between the fluid sections 51, 53, and tests have shown that a current may be completely prevented (i.e. full limitation is obtained) by the air-injection. Suitable sizes of the air gaps and suitable intervals of injection (size of and distance between the air gaps) may be empirically determined.

Other embodiments that provide an air gap are conceivable. For example, it is possible to arrange an air inlet in the downstream fluid line and a suction pump downstream the air inlet. The suction pump is then operated to provide a flow rate that is greater than a flow rate of treatment fluid from the fluid source, such that air is drawn into the fluid line from the air inlet and mixed with the treatment fluid. The air mixed with the treatment fluid separates the treatment fluid into a number of sections, and sufficient electrical isolation can be obtained by drawing in e.g. twice as much air from the air inlet as treatment fluid from the fluid source.

Figure 7:
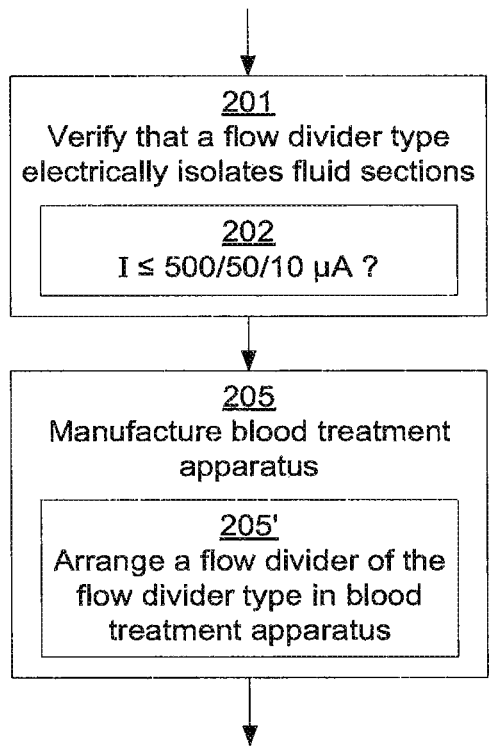
FIG. 7 is a flow chart of a method for verifying that a flow divider electrically isolates two fluid sections, in combination with a method for manufacturing a blood treatment apparatus.

With reference to FIG. 7 a method of manufacturing any of the embodiments of the blood treatment apparatus described above is illustrated. The method comprises the step 205 of manufacturing the blood treatment apparatus 2 which is done according to known techniques, but includes the step 205' of arranging in the blood treatment apparatus any of the flow dividers described above. However, the step 205 of manufacturing the blood treatment apparatus is always preceded by a step 201 of verifying that the flow divider is of a type that electrically isolates the fluid sections.

The step of verification 201 includes verifying that the flow divider electrically isolates the fluid sections such that the electrical current is limited to maximum any of 500 μA, 50 μA and 10 μA. The verification may be done by using the test equipment of FIG. 2a.

Since the verification is an important step when manufacturing the blood treatment apparatus, it may be said that the verification is a part of the manufacturing process even though it must not be performed before every step of manufacturing a blood treatment apparatus. It suffices that the step 201 of verification is performed once for the type of flow divider that is used. After the step 201 of verification the step 205 of manufacturing a blood treatment apparatus may be performed numerous times.

Figure 8:
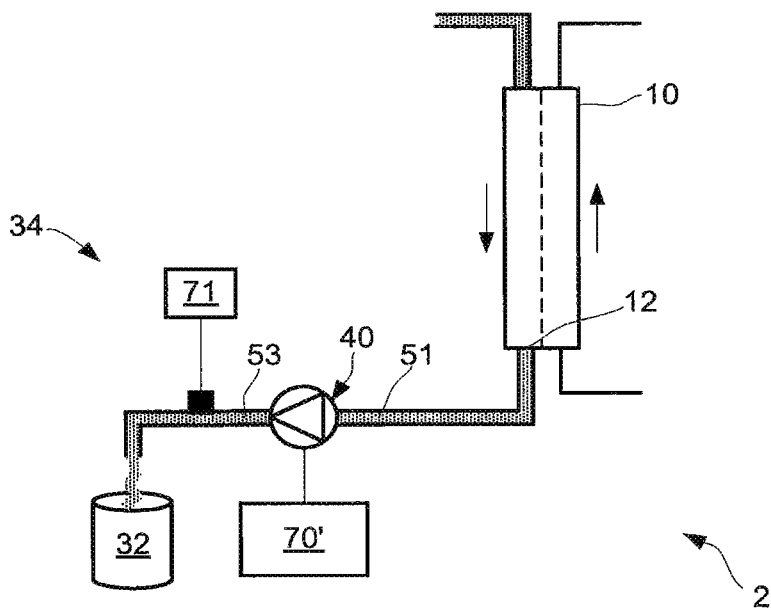
FIG. 8 illustrates an embodiment of a blood treatment apparatus configured to detect a leakage current.

With reference to FIG. 8 the downstream fluid line 34 of an alternative blood treatment apparatus is illustrated. Reference numerals similar with reference numerals in other figures represent similar items. The blood treatment apparatus 2 includes a grounding device 71 that is connected to the downstream fluid line 34 and which may disconnect the grounding connection if a leakage current measured on a patient connected to the blood treatment apparatus exceeds a predetermined value.

If the leakage current exceeds the predetermined value then the control device 70' activates a flow divider 40 (e.g. in form of a pump, valve or clamp) such that the treatment fluid in the fluid line is separated into to the fluid sections 51, 53. Patent document WO 2009/044220 exemplifies how leakage current may be measured, and is incorporated by reference.

The control unit 60 and the control device 70 described herein typically includes a respective one or more processing units that may execute software instructions, i.e. computer program code that carry out the above described operations. For this purpose the blood treatment apparatus may include a computer-readable memory that stores the software instructions. These may for development convenience be written in a high-level programming language such as Java, C, and/or C++ but also in other programming languages, such as, but not limited to, interpreted languages. Also, the control unit 60 and the control device 70 may be embodied as a single unit.

Moreover, the flow divider and any parts that support its function, including the connectors, may just as well be arranged in the upstream fluid line. However, it is generally more advantageous to have the flow divider in the downstream fluid line, since it is then closer to the sink. For increasing the level of electrical insulation it is possible to arrange several flow dividers in the fluid line. The flow dividers may then be of the same type or of different types. Several flow dividers in combination may be seen as one flow divider.

Although various embodiments of the invention have been described and shown, the invention is not restricted thereto, but may also be embodied in other ways within the scope of the subject-matter defined in the following claims.

What is claimed is:

1. A blood treatment apparatus comprising:
   a blood treatment unit including a fluid inlet and a fluid outlet;
   a blood line configured to extract blood from a blood source, pass the blood through the blood treatment unit, and deliver treated blood to a target vessel;
   a fluid line including
      an upstream fluid line configured to receive electrically conductive treatment fluid from a fluid source and pass the electrically conductive treatment fluid to the fluid inlet of the blood treatment unit such that the electrically conductive treatment fluid interacts with the blood within the blood treatment unit to form used electrically conductive treatment fluid, and
      a downstream fluid line connected to the fluid outlet of the blood treatment unit for delivering the used electrically conductive treatment fluid to a fluid sink; and
   a flow divider arranged in the downstream fluid line and configured to separate the used electrically conductive treatment fluid in the downstream fluid line into to a first fluid section and a second fluid section, thereby electrically isolating the first and second fluid sections such that electrical current flowing in the first fluid section is prevented from reaching the second fluid section.

2. The blood treatment apparatus of claim 1, wherein the flow divider is configured to separate the used electrically conductive treatment fluid in the downstream fluid line into multiple fluid sections, including at least the first and second fluid sections, thereby breaking up a flow of the used electrically conductive treatment fluid in the downstream fluid line.

3. The blood treatment apparatus of claim 1, wherein the flow divider is configured to provide a gas gap in the downstream fluid line for generating separation of the used electrically conductive treatment fluid in the downstream fluid line.

4. The blood treatment apparatus of claim 1, wherein the flow divider is configured to periodically open and close the downstream fluid line for generating separation of the used electrically conductive treatment fluid in the downstream fluid line.

5. The blood treatment apparatus of claim 1, wherein the flow divider includes a drip chamber for generating separation of the used electrically conductive treatment fluid in the downstream fluid line.

6. The blood treatment apparatus of claim 1, wherein the flow divider includes a first opening device and a second opening device, the first and second opening devices configured to periodically open and close the downstream fluid line for generating separation of the used electrically conductive treatment fluid in the downstream fluid line.

7. The blood treatment apparatus of claim 6, wherein at least one of the first and second opening devices includes a clamp.

8. The blood treatment apparatus of claim 6, wherein at least one of the first and second opening devices includes a valve.

9. The blood treatment apparatus of claim 1, wherein the flow divider includes a peristaltic pump.

10. The blood treatment apparatus of claim 9, wherein the peristaltic pump includes at least two rollers configured to periodically compress the downstream fluid line.

11. The blood treatment apparatus of claim 1, wherein the flow divider is configured to electrically isolate the first and second fluid sections such that the electrical current is limited to a predetermined value that is between 10 μA and 500 μA.

12. The blood treatment apparatus of claim 1, further comprising a buffer chamber configured to cooperate with the flow divider for generating separation of the used electrically conductive treatment fluid in the downstream fluid line.

13. The blood treatment apparatus of claim 1, further comprising a control unit configured to verify if the electrical current flows between the first and second fluid sections.

14. The blood treatment apparatus of claim 13, wherein the control unit includes a first connector arranged in the downstream fluid line upstream of the flow divider at the first fluid section and a second connector arranged in the downstream fluid line downstream of the flow divider at the second fluid section.

15. The blood treatment apparatus of claim 14, wherein the control unit is configured to:
  apply a voltage over at least one of the first and second connectors;
  determine a value of the electrical current ($I_t$) flowing in the used electrically conductive treatment fluid between the first and second connectors;
  compare the value of the electrical current ($I_t$) to a predetermined current value; and
  when the value of the electrical current ($I_t$) exceeds the predetermined current value, at least one of
    cause a power interruption to at least a portion of the blood treatment apparatus,
    break a power supply to the blood treatment apparatus, or
    provide an indication that the flow divider is not providing electrical isolation.

16. The blood treatment apparatus of claim 14, wherein the control unit is configured to:
  apply the electrical current through at least one of the first and second connectors;
  determine a value of the electrical current ($I_t$) flowing in the used electrically conductive treatment fluid between the first and second connectors;
  compare the value of the electrical current ($I_t$) to a predetermined current value; and
  when the value of the electrical current ($I_t$) exceeds the predetermined current value, at least one of
    cause a power interruption to at least a portion of the blood treatment apparatus,
    break a power supply to the blood treatment apparatus, or
    provide an indication that the flow divider is not providing electrical isolation.

17. The blood treatment apparatus of claim 14, wherein the control unit is configured to:
  apply the electrical current through at least one of the first and second connectors;
  determine a voltage differential between the first and second connectors;
  compare the voltage differential to a predetermined voltage value; and
  when the voltage differential is less than the predetermined voltage value, at least one of
    cause a power interruption to at least a portion of the blood treatment apparatus,
    break a power supply to the blood treatment apparatus, or
    provide an indication that the flow divider is not providing electrical isolation.

18. The blood treatment apparatus of claim 1, wherein the electrically conductive treatment fluid is dialysate and the used electrically conductive treatment fluid is used dialysate.

19. The blood treatment apparatus of claim 1, further comprising the fluid sink,
  wherein the fluid sink is electrically connected to an electrical ground.

20. The blood treatment apparatus of claim 19, wherein the fluid sink includes at least one of a drain or a sewer.

* * * * *